US00PP11189P

United States Patent [19]

Kordes

[11] Patent Number: Plant 11,189

[45] Date of Patent: Jan. 25, 2000

[54] HYBRID TEA ROSE PLANT NAMED 'KORVECO'

[75] Inventor: Wilhelm Kordes, Sparrieshoop, Germany

[73] Assignee: Bear Creek Gardens, Inc., Medford, Oreg.

[21] Appl. No.: 09/045,195

[22] Filed: Mar. 20, 1998

[51] Int. Cl.[7] ..... A01H 5/00

[52] U.S. Cl. ..... Plt./136

[58] Field of Search ..... Plt./130, 135, 136, Plt./139

*Primary Examiner*—Howard J. Locker

*Attorney, Agent, or Firm*—Klarquist Sparkman Campbell Leigh & Whinston

[57] ABSTRACT

Hybrid tea rose plant having good production of flowers having a strong, stable color on long stems; the flowers having thick petals and long vase life.

1 Drawing Sheet

The present invention relates to a new and distinct variety of rose plant of the hybrid tea class which was originated by me by crossing an unnamed pink seedling (not patented), the parentage of which is not known, with 'KORxenna' (U.S. Plant Pat. No. 7,510).

The primary objective of this breeding was to produce a new rose variety having the good cut flower production and long vase life, of the unnamed, pink, cut flower female seedling, combined with the long stems, good flower color and good shipping ability of the male parent. The objective was substantially achieved, along with other desirable improvements, as evidenced by the following unique combination of characteristics that are outstanding in the new variety and that distinguish it from its parents, as well as from all other varieties of which I am aware:

1. Long vase life;
2. Strong, stable flower color;
3. Thick petals;
4. Good shipping ability;
5. Long, straight stems;
6. Good cut flower production—160–170 stems per square meter of greenhouse, or 23–24 stems per plant per year.

Asexual reproduction of this new variety by budding, as performed at Wasco, Calif. and Sparrieshoop, Germany, shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed pink seedling (not patented), the parentage of which is not known.

*Pollen parent.*—'KORxenna' (U.S. Plant Pat. No. 7,510).

Classificiation:

*Botanical.*—Rosa hybrida.

*Commercial.*—Hybrid tea.

FLOWER

Observations made from specimens grown in a greenhouse environment at Somis, Calif. and Sparrieshoop, Germany.

Blooming Habit: Continuous.

Bud:

*Size.*—1¾" long when the petals start to unfurl.

*Form.*—Long, pointed ovoid.

*Color.*—When sepals first divide, bud color is Red Group 44D. When half blown, the upper sides of the petals are Red Group 40D, the lower sides of the petals are Red Group 44D.

*Sepals.*—Color: Green Group 138B. Surface Texture: Covered in fine hairs. There are three lightly appendaged sepals. There are two unappendaged sepals with hairy edges.

*Receptacle.*—Color: Green Group 143C. Shape: Funnel. Size: Large (9/16"×5/16"). Surface: Smooth.

*Peduncle.*—Length: Medium (3½ to 3¾"), Surface: Smooth, with some glands. Color: Medium green. Strength; Stiff, erect, heavy.

Bloom:

*Size.*—Large. Average open size is 4 to 4½".

*Borne.*—Singly.

*Stems.*—Long (22–26"), strong.

*Form.*—When first open: High centered. Permanence: Retains its form to the end, outer petals curl back.

*Petalage.*—Number of petals under normal conditions: 25–30.

*Color.*—The upper sides of the petals are Red Group 40B. The reverse sides of the petals are Red Group 44D. The base of each petal has a small (⅜"×¼") Yellow Group 4D half moon at the point of attachment. The major color on the upper sides is Red Group 40B.

*Variegations.*—Occasional greenish-white streak on the guard petals.

*Discoloration.*—At the end of the first day: No change. At the end of the third day: No Change. No change through days twelve–fourteen, in the vase.

*Fragrance.*—Slight.

Petals:

*Texture.*—Thick, leathery.

*Shape.*—Round.

*Form.*—Tips slightly recurved.

*Arrangement.*—Imbricated. Petaloids in the center are few.
*Persistence.*—Petals drop off cleanly before drying.
*Lastingness.*—On the plant: Long (8–9 days). As a cut flower: Very long (12–14 days).

Reproductive parts:
*Anthers.*—Size: Medium. Quantity: Many. Color: Yellow. Arrangement: Regular around styles.
*Filaments.*—Color: Light reddish pink.
*Pollen.*—Color: Lemon yellow.
*Styles.*—Color: Reddish pink.
*Stigmas.*—Color: Greenish white.

Plant:
*Form.*—Bush.
*Growth.*—Very vigorous: upright; branching: Height is six feet, width is three and one-half feet in the greenhouse after six months. It is then maintained at this size by regular cutting.

Foliage: Number of leaflets on normal mid-stem leaves: Five
*Size.*—Large (6½"×5¼").
*Quantity.*—Abundant.
*Color.*—New foliage: Upper and lower sides: Greyed Red Group 178A. Old foliage: Upper side: Green Group 137A. Lower side: Green Group 138B.

Leaflets:
*Shape.*—Pointed oval.
*Texture.*—Upper side: Leathery, smooth.
*Edge.*—Serrated.
*Serration.*—Single, small.
*Petiole rachis.*—Color: Reddish.
*Petiole underside.*—Smooth with occasional prickles.
*Stipules.*—Medium (½" to ⅝"), bearded.
*Disease Resistance.*—Resistant to mildew under normal growing conditions at Somis, Calif. and Sparrieshoop, Germany.

Wood:
*New wood.*—Color: Reddish. Bark: Smooth
*Old wood.*—Color: Green. Bark: Smooth.

Prickles:
*Quantity.*—On main canes from base: Ordinary. On laterals from main canes: Ordinary.
*Form.*—Medium (¼" to 5/16"); hooked downward.
*Color when young.*—Red.

Small Prickles:
*Quantity.*—On main stalks: Few. On laterals: Few.
*Color.*—Red.

I claim:

1. A new and distinct variety of rose plant of the hybrid tea class, as herein shown and described, characterized particularly by its good production of flowers having strong, stable color and long, straight stems; the flowers having thick petals and long vase life.

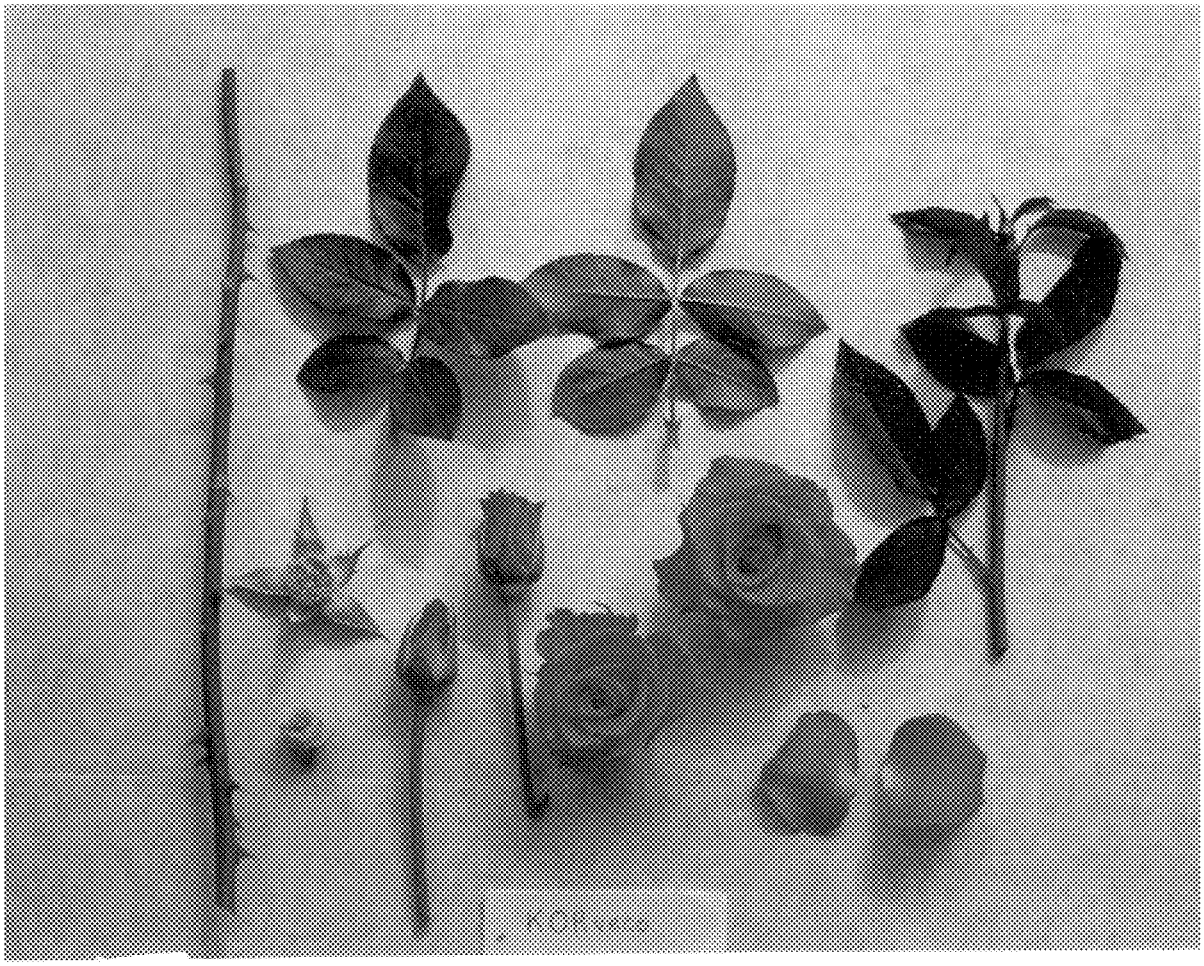

* * * * *